United States Patent
Strauss et al.

(10) Patent No.: US 7,018,365 B2
(45) Date of Patent: Mar. 28, 2006

(54) THREADED SYRINGE WITH QUICK STOP

(75) Inventors: Brian M. Strauss, Trabuco Canyon, CA (US); Brock H. Smith, So. Pasadena, CA (US); Brian Canfield, Costa Mesa, CA (US); Amanda Conner, Rancho Santa Margarita, CA (US); Douglas R. Hayman, Mission Viejo, CA (US); Ed Olsen, Lake Forest, CA (US)

(73) Assignee: Micro Therapeutics, Inc., Irvine, CA (US)

( * ) Notice: Subject to any disclaimer, the term of this patent is extended or adjusted under 35 U.S.C. 154(b) by 0 days.

(21) Appl. No.: 10/222,478

(22) Filed: Aug. 16, 2002

(65) Prior Publication Data

US 2003/0055386 A1 Mar. 20, 2003

Related U.S. Application Data

(63) Continuation-in-part of application No. 09/574,500, filed on May 19, 2000, now Pat. No. 6,645,167.

(60) Provisional application No. 60/135,289, filed on May 21, 1999, provisional application No. 60/135,222, filed on May 21, 1999.

(51) Int. Cl.
*A61M 5/00* (2006.01)
*A61M 5/245* (2006.01)
*B67D 5/42* (2006.01)

(52) U.S. Cl. ............... 604/211; 604/210; 604/207; 604/232; 604/110; 222/390

(58) Field of Classification Search ........ 604/110–222, 604/232, 99.01, 224, 509, 28, 263, 578; 222/390

See application file for complete search history.

(56) References Cited

U.S. PATENT DOCUMENTS

| 4,200,804 A | | 4/1980 | Farella et al. |
| 4,244,366 A | * | 1/1981 | Raines ................. 604/211 |
| 4,710,179 A | * | 12/1987 | Haber et al. .......... 604/211 |
| 4,938,763 A | | 7/1990 | Dunn et al. |
| 4,944,726 A | | 7/1990 | Hilal et al. |

(Continued)

FOREIGN PATENT DOCUMENTS

EP 0 291 177 A2 4/1988

(Continued)

OTHER PUBLICATIONS

Aletich, et al., "The Remodeling Technique of Balloon-Assisted Guglielmi Detachable Coil Placement in Wide-Necked Anuerysms: Experience at the University of Illinois at Chicago", *J. Neurosurg*, 93:388-396 (2000).

(Continued)

*Primary Examiner*—Nicholas D. Lucchesi
*Assistant Examiner*—Roz Maiorino
(74) *Attorney, Agent, or Firm*—Foley & Lardner LLP

(57) ABSTRACT

A threaded syringe provides a mechanism by which a clinician can deliver a viscous fluid through a relatively small lumen and can obtain tactile or audible feedback of delivery. The threaded syringe allows for delivery of more viscous fluids with less force and/or allows for more controlled delivery. The syringe includes a syringe barrel and a sliding member positioned on the proximal end of the syringe barrel. The sliding member has a first threaded hole and a second hole. The sliding member is slidable on the syringe barrel between a first position at which the first threaded hole is aligned with the syringe barrel for precise delivery of a material from the syringe and a second position at which the second hole is aligned with the syringe barrel for filling of the syringe or to stop bleed out.

7 Claims, 4 Drawing Sheets

U.S. PATENT DOCUMENTS

| | | | |
|---|---|---|---|
| 4,983,585 | A | 1/1991 | Pennell et al. |
| 5,068,225 | A | 11/1991 | Pennell et al. |
| 5,084,017 | A * | 1/1992 | Maffetone ............ 604/110 |
| RE33,821 | E | 2/1992 | Banks |
| 5,116,615 | A | 5/1992 | Gokcen et al. |
| 5,147,294 | A | 9/1992 | Smith et al. |
| 5,250,030 | A | 10/1993 | Corsich |
| 5,256,144 | A | 10/1993 | Kraus et al. |
| 5,324,263 | A | 6/1994 | Kraus et al. |
| 5,385,561 | A | 1/1995 | Cerny |
| 5,389,076 | A * | 2/1995 | Shaw ............ 604/110 |
| 5,433,216 | A | 7/1995 | Sugrue et al. |
| 5,466,680 | A | 11/1995 | Rudy |
| 5,469,867 | A | 11/1995 | Schmitt |
| 5,526,809 | A | 6/1996 | Fiddian-Green |
| 5,540,657 | A | 7/1996 | Kurjan et al. |
| 5,561,134 | A | 10/1996 | Spada et al. |
| 5,580,568 | A | 12/1996 | Greff et al. |
| 5,582,167 | A | 12/1996 | Joseph |
| 5,611,783 | A * | 3/1997 | Mikkelsen ............ 604/208 |
| 5,618,273 | A * | 4/1997 | Fischer ............ 604/211 |
| 5,650,447 | A | 7/1997 | Keefer et al. |
| 5,651,980 | A | 7/1997 | Lanza et al. |
| 5,652,366 | A | 7/1997 | Spada et al. |
| 5,661,171 | A | 8/1997 | Acharya |
| 5,667,767 | A | 9/1997 | Greff et al. |
| 5,695,480 | A | 12/1997 | Evans et al. |
| 5,731,338 | A | 3/1998 | Acharya |
| 5,736,554 | A | 4/1998 | Spada et al. |
| 5,741,275 | A | 4/1998 | Wyssmann |
| 5,741,805 | A | 4/1998 | Acharya |
| 5,749,968 | A | 5/1998 | Melanson et al. |
| 5,776,096 | A | 7/1998 | Fields |
| 5,800,373 | A | 9/1998 | Melanson et al. |
| 5,819,723 | A | 10/1998 | Joseph |
| 5,824,703 | A | 10/1998 | Clark, Jr. |
| 5,826,584 | A | 10/1998 | Schmitt |
| 5,830,178 | A | 11/1998 | Jones et al. |
| 5,844,016 | A | 12/1998 | Sawhney et al. |
| 5,851,508 | A | 12/1998 | Greff et al. ............ 424/9.411 |
| 5,888,546 | A | 3/1999 | Ji et al. |
| 5,891,477 | A | 4/1999 | Lanza et al. |
| 5,894,022 | A | 4/1999 | Ji et al. |
| 5,902,796 | A | 5/1999 | Shand et al. |
| 5,910,104 | A | 6/1999 | Dobak, III et al. |
| 5,912,005 | A | 6/1999 | Lanza et al. |
| 5,945,102 | A | 8/1999 | de Faire et al. |
| 5,952,351 | A | 9/1999 | Evans et al. |
| 5,958,406 | A | 9/1999 | de Faire et al. |
| 5,964,223 | A | 10/1999 | Baran |
| 5,981,698 | A | 11/1999 | Brittain |
| 6,030,612 | A | 2/2000 | de Faire et al. |
| 6,090,945 | A | 7/2000 | Audia et al. |
| 6,096,763 | A | 8/2000 | Hoffman et al. |
| 6,099,499 | A | 8/2000 | Ciamacco, Jr. |
| 6,117,142 | A | 9/2000 | Goodson et al. |
| 6,121,341 | A | 9/2000 | Sawhney et al. |
| 6,126,936 | A | 10/2000 | Lanza et al. |
| 6,130,200 | A | 10/2000 | Brodbeck et al. |
| 6,171,298 | B1 | 1/2001 | Matsuura et al. |
| 6,183,461 | B1 | 2/2001 | Matsuura et al. |
| 6,258,819 | B1 | 7/2001 | Clark et al. |
| 6,261,582 | B1 | 7/2001 | Needham et al. |
| 6,287,558 | B1 | 9/2001 | Lanza et al. |
| 6,291,528 | B1 | 9/2001 | Scott |
| 6,296,847 | B1 | 10/2001 | Gokcen et al. |
| 6,307,054 | B1 | 10/2001 | Truesdale et al. |
| 6,331,311 | B1 | 12/2001 | Brodbeck et al. |
| 6,335,384 | B1 | 1/2002 | Evans et al. |
| 6,368,612 | B1 | 4/2002 | Lanza et al. |
| 6,376,500 | B1 | 4/2002 | Clark et al. |
| 6,387,977 | B1 | 5/2002 | Sawhney et al. |

FOREIGN PATENT DOCUMENTS

| | | |
|---|---|---|
| WO | WO 90/03768 | 4/1990 |
| WO | WO 98/04312 | 2/1998 |
| WO | WO 99/20326 | 4/1999 |
| WO | 00/71196 A1 | 11/2000 |

OTHER PUBLICATIONS

Casarett and Doull's *Toxicology*, Amdur et al., Editors, Pergamon Press, New York, pp. 661-664 (1975).

Cognard, et al., "Treatment of Distal Aneurysms of the Cerebellar Arteries by Intraaneurysmal Injection of Glue", *Am. J. Neuroradiol.*, 20:780-784 (1999).

Kinugasa, et al., "Direct Thrombosis of Aneurysms with Cellulose Acetate Polymer", *J. Neurosurg.*, 77:501-507 (1992).

Kinugasa, et al., "Early Treatment of Subarachnoid Hemorrhage After Preventing Rerupture of an Aneurysm", *J. Neurosurg.*, 83:34-41 (1995).

Kinugasa, et al., "Prophylactic Thrombosis to Prevent New Bleeding and to Delay Aneurysm Surgery", *Neurosurg.*, 36:661 (1995).

Malek, et al., "Balloon-assist Technique for Endovascular Coil Embolization of Geometrically Difficult Intracranial Aneurysm", *Neurosurgery*, 46(6):1397-1407 (2000).

Mandai, et al., "Direct Thrombosis of Aneurysms with Cellulose Acetate Polymer", *J. Neurosurg.*, 77:497-500 (1992).

Moret, et al., "The "Remodeling Technique" in the Treatment of Wide Neck Intracranial Aneurysms", *Interventional Neuroradiology*, 3:21-35 (1997).

Nelson, et al., "Balloon-assisted Coil Embolization of Wide-Necked Aneurysms of the Internal Carotid Artery: Medium-term Angiographic and Clinical Follow-up in 22 Patients", *Am J. Neuroradiol.*, 22:19-26 (2001).

Pierot, et al., "Endovascular Treatment of Post-Traumatic Complex Carotid-Cavernous Fistulas, Using the Arterial Approach", *J. Neuroradiol.*, 19:79-87 (1992) (document presented in both English and French).

Riina, et al., "Future Endovascular Management of Cerebral Aneurysms", *Neurosurgery Clinics of North America*, 9(4):917-921 (1998).

Taki, et al., "Selection and Combination of Various Endovascular Techniques in the Treatment of Giant Aneurysms", *J. Neurosurg.*, 77:37-42 (1992).

Weill, et al., "Giant Aneurysms of the Middle Cerebral Artery Trifurcation Treated with Extracranial-Intracranial Arterial Bypass and Endovascular Occlussion", *J. Neurosurg.*, 89:474-478 (1998).

Yamashita, et al. "Characteristics of Ethylene Vinyl Alcohol Copolymer (EVAL) Mixtures", AJNR Am. J. Neuroadiology, 15:1103-1105 (1994).

\* cited by examiner

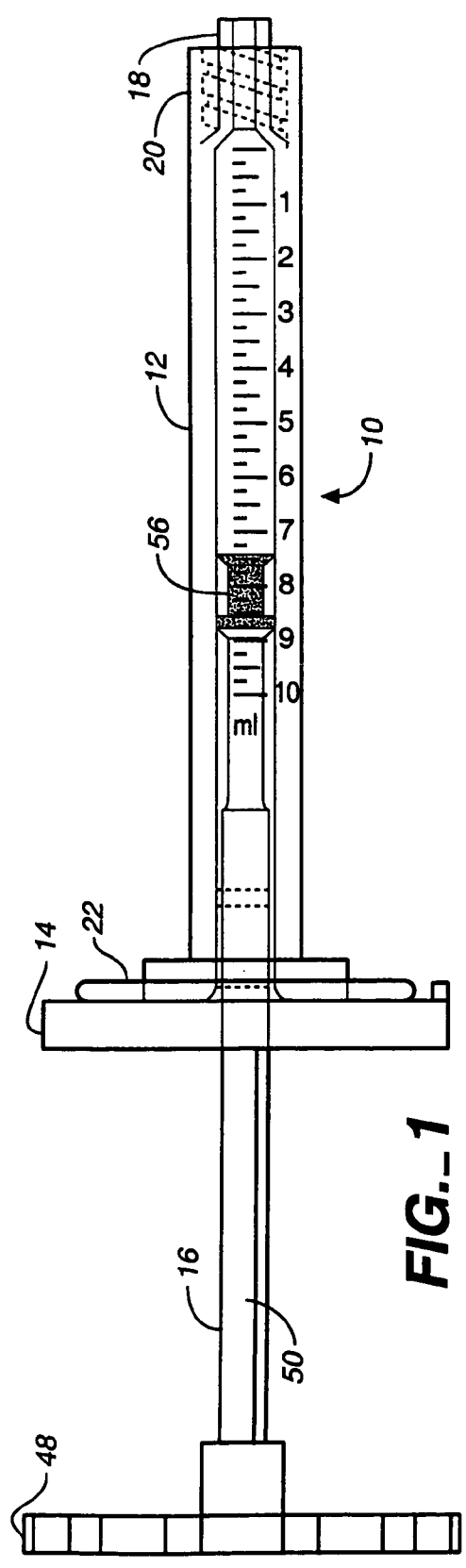
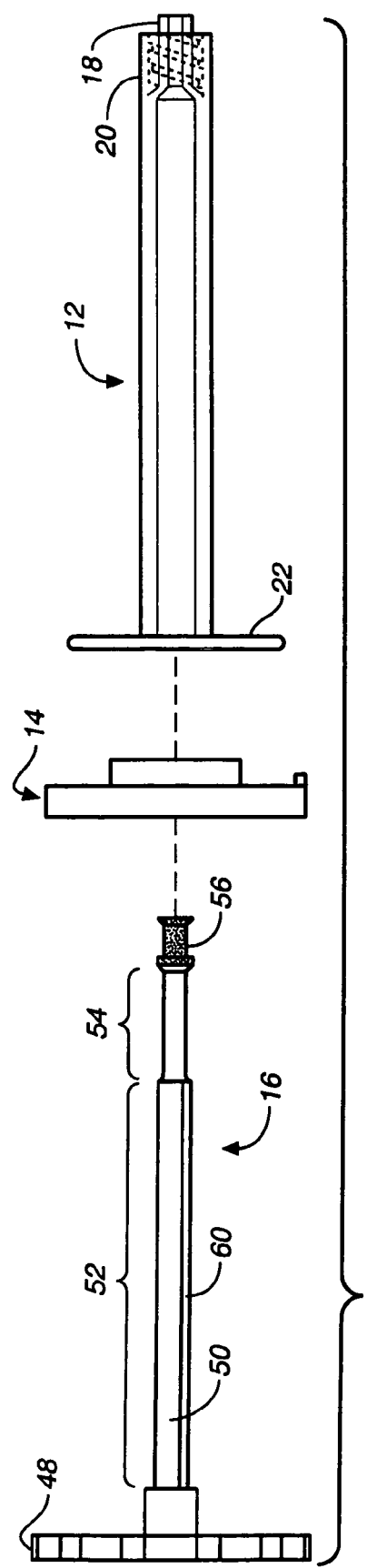

FIG._2A
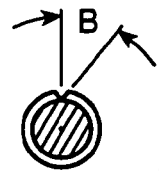
FIG._2B
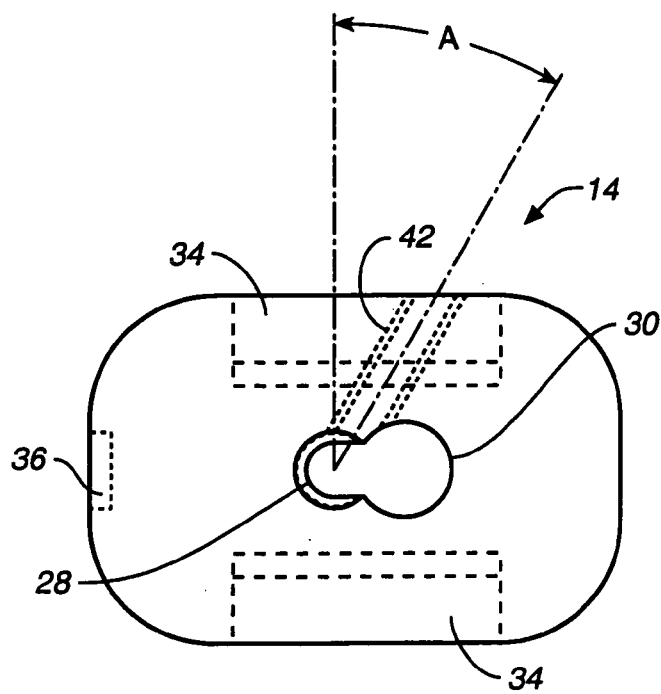
FIG._3
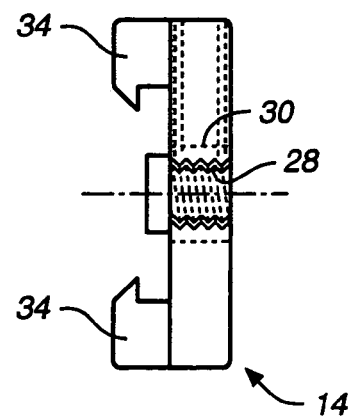
FIG._4
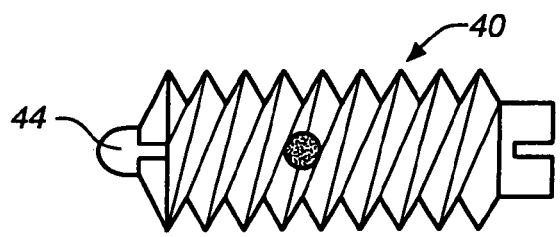
FIG._5

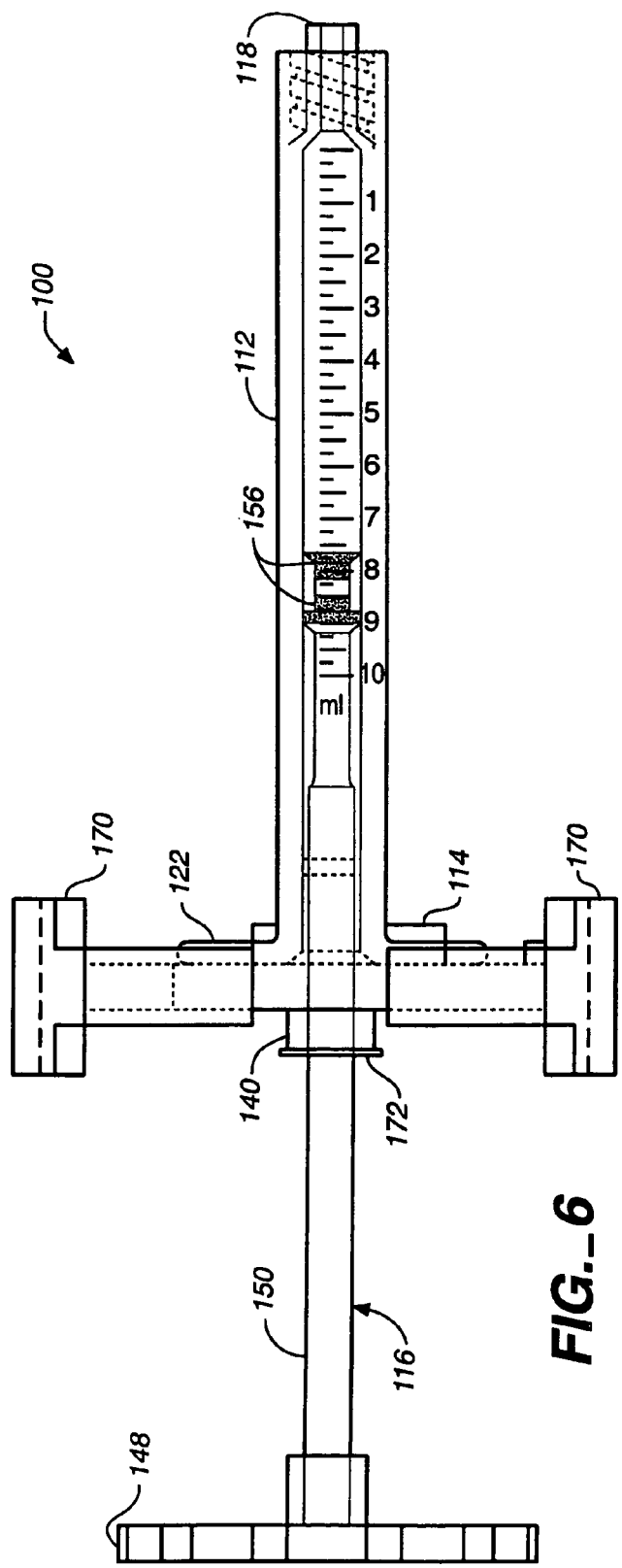
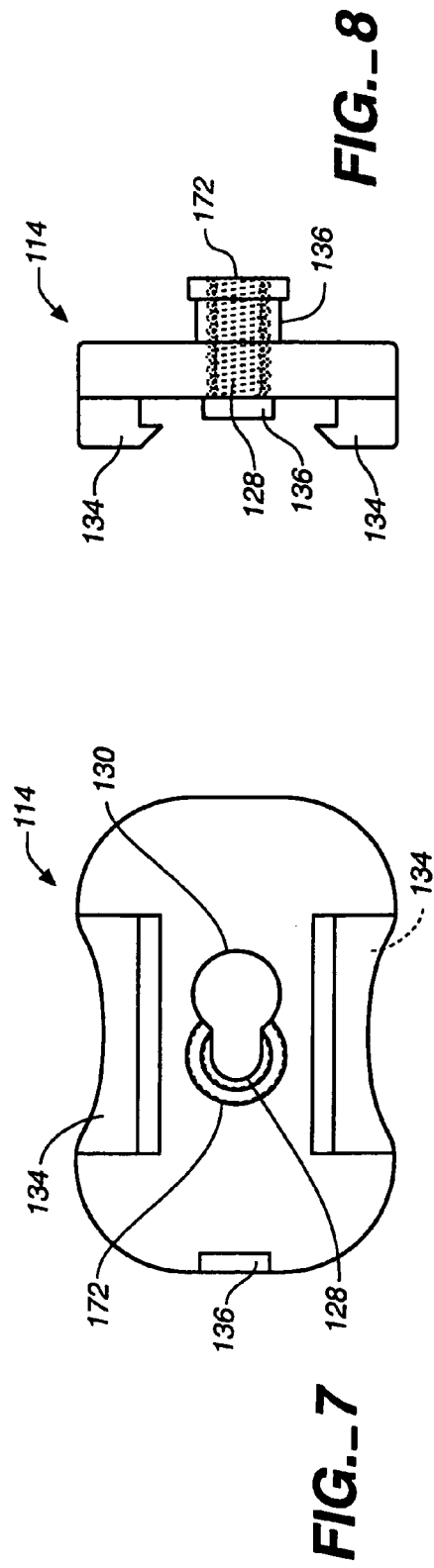
FIG._6
FIG._7
FIG._8

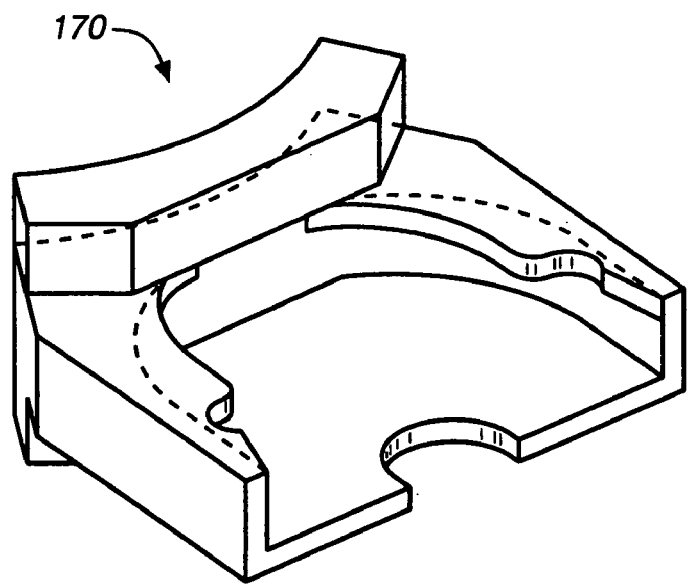
FIG._9
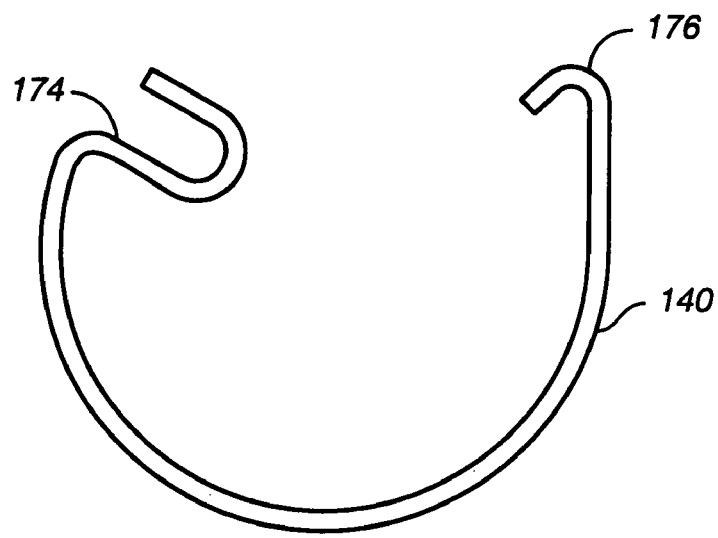
FIG._10

THREADED SYRINGE WITH QUICK STOP

CROSS-REFERENCE TO RELATED APPLICATIONS

This application is a continuation-in-part of U.S. patent application Ser. No. 09/574,500 filed on May 19, 2000 now U.S. Pat. No. 6,645,167 which claims benefit of U.S. Provisional Patent Application Ser. No. 60/135,222 filed May 21, 1999, and U.S. Provisional Patent Application Ser. No. 60/135,289 filed May 21, 1999, which are incorporated herein by reference in their entirety.

BACKGROUND OF THE INVENTION

1. Field of the Invention

The invention relates to a threaded syringe, and more particularly, the invention relates to a threaded syringe with a quick stop.

2. Brief Description of the Related Art

The delivery of fluid compositions which solidify in vivo is particularly useful for a variety of reasons including treatment of blood vessels, tumors, aneurysms, arteriovenous malformations ("AVMs"), arteriovenous fistula ("AVF"), uncontrolled bleeding and the like, as well as in the sterilization of mammals by blocking the vas deferens or fallopian tubes, in the treatment of urinary incontinence by the addition of a bulking agent to the periurethral tissue, and the like.

Delivery of such compositions is preferably accomplished via catheter techniques which permit the selective placement of the catheter at the delivery site. For example, recent advancements in catheter technology as well as in angiography now permit neuro endovascular intervention including the treatment of otherwise inoperable lesions. Specifically, development of microcatheters and guidewires capable of providing access to vessels as small as 1 millimeter in diameter allows for the endovascular treatment of many lesions.

Catheter delivery for in vivo solid mass formation can employ fluid compositions which comprise a solvent such as ethanol, dimethylsulfoxide ("DMSO"), or aqueous solutions of ethanol or DMSO, a biocompatible water insoluble polymer, and a water insoluble contrast agent. Preferably, however, the solvent is non-aqueous in order to maximize the amount of biocompatible water insoluble polymer which can be dissolved therein.

In practice, the catheter tip is directed to the vascular or other delivery site by use of conventional visualization techniques such as fluoroscopy, and the like which allow the clinician to visualize the catheter tip. After placement of the catheter, the composition is introduced into the catheter and delivered to this site. Upon delivery, the solvent dissipates into the blood, fluid, or tissue and the water insoluble polymer precipitates to form a coherent mass which solidifies in vivo.

One use of this liquid embolic polymer composition is in minimally invasive procedures for treating intracranial aneurysms. The use of liquid embolic compositions addresses the problems with the known aneurysm treatment methods, such as surgical clipping and coil delivery, and involves the endovascular injection of the liquid embolic composition which solidifies in the aneurysm to occlude the aneurysm. Typically, the liquid embolic composition will include a water insoluble, biocompatible, non-biodegradable polymer dissolved in a biocompatible solvent. Once the liquid embolic composition is injected into the aneurysm, the biocompatible solvent dissipates into the blood and the polymer solidifies to occlude the blood flow into the aneurysm. These liquid embolic compositions preferably include a radiopaque material which allows the physician to view the embolization procedure by fluoroscopy or other visualization techniques.

Due to limitations of the conventional catheter delivery systems for delivery of these liquid embolic compositions, it was difficult to deliver compositions of a biocompatible polymer, a biocompatible solvent, and a biocompatible contrast agent including greater than 8 weight percent polymer based on the entire weight of the compositions, through a micro catheter with a conventional syringe because of the viscosity of the composition. However, in some instances it is desirable to deliver higher viscosity embolic compositions, for example compositions containing more than 8 weight percent of a polymer. Higher viscosity embolic compositions are described in U.S. patent application Ser. No. 09/574,379 entitled "Novel High Viscosity Embolizing Compositions," filed May 19, 2000, which is incorporated herein by reference in its entirety. These higher viscosity embolic compositions are generally easier to position within an aneurysm. The higher viscosity may also help to prevent portions of the polymer from being separated from polymer mass and being carried away in the blood stream where the polymer can occlude an undesired vascular location.

Accordingly, it would be desirable to provide a syringe for delivery of high viscosity liquids through small lumens.

It would also be desirable to provide a syringe with a tactile or audible indication of delivery which allows the clinician to monitor delivery without viewing the syringe.

It would also be desirable to provide a threaded syringe with a quick stop mechanism for releasing pressure on the delivered fluid to rapidly stop delivery of the fluid.

SUMMARY OF THE INVENTION

According to one aspect of the present invention, a syringe includes a syringe barrel having a distal delivery orifice and a proximal end, a sliding member positioned on the proximal end of the syringe barrel, the sliding member having a first threaded hole and a second hole and being slidable on the syringe barrel between a first position at which the first threaded hole is aligned with the syringe barrel and a second position at which the second hole is aligned with the syringe barrel, and a threaded plunger for delivery of a fluid from the syringe barrel through the delivery orifice.

According to another aspect of the present invention, a method for embolizing a vascular site includes the steps of positioning the distal end of a delivery catheter in said vascular site, connecting a threaded syringe containing a liquid embolic composition to a distal end of the delivery catheter, rotating a plunger of the threaded syringe to inject the liquid embolic composition to the vascular site in a precisely controllable manner, and releasing pressure on the liquid embolic composition by disengaging threads of the plunger from a barrel of the syringe.

According to a further aspect of the present invention, a syringe includes a syringe barrel having a distal delivery orifice and a proximal end, an internally threaded member at the proximal end of the syringe barrel, a threaded plunger receivable in the internally threaded member for delivery of a fluid from the syringe barrel through the delivery orifice, the threaded plunger having a longitudinal groove, and a spring element for engaging the longitudinal groove to provide a tactile or audible indication of fluid delivery.

The present invention provides advantages of a syringe which can be used to deliver a high viscosity composition. The invention may also be used as either a conventional syringe or a threaded syringe. The present invention may also provide a quick stop mechanism for stopping the delivery of a high viscosity composition. The present invention may also provide the advantage of a tactile or audible indication of delivery.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 1 is a side view of the syringe according to the present invention;

FIG. 2 is an exploded side view of the syringe of FIG. 1;

FIG. 2A is an end view of the proximal end of the syringe barrel;

FIG. 2B is an enlarged cross sectional view of the plunger shaft;

FIG. 3 is a is a top view of a sliding end member of the syringe;

FIG. 4 is a side view of the sliding end member of FIG. 3;

FIG. 5 is an enlarged side view of the spring element;

FIG. 6 is a side view of an alternative embodiment of a syringe according to the invention;

FIG. 7 is a bottom view of the sliding end member of the syringe of FIG. 6;

FIG. 8 is a side view of the sliding end member of FIG. 7;

FIG. 9 is a perspective view of a thumb pad of the syringe of FIG. 6; and

FIG. 10 is a top view of a spring clip of the syringe of FIG. 6.

DETAILED DESCRIPTION OF THE PREFERRED EMBODIMENTS

A syringe according to the present invention provides a mechanism by which a clinician can deliver a viscous fluid through relatively small lumens and can obtain tactile or audible feedback of delivery. According to one aspect of the invention, the syringe can be used either as a conventional syringe or as a threaded syringe. The threaded syringe allows for delivery of more viscous fluids with less force and/or allows for more controlled delivery. The threaded syringe is particularly useful for delivery of fluids through small diameter lumens such as micro catheters. Micro catheters typically have lumen diameters of about 0.008 inches to about 0.018 inches.

FIG. 1 shows a syringe assembly 10 according to the present invention which includes a syringe barrel 12, a sliding member 14, and a threaded plunger 16. The syringe barrel 12, as shown most clearly in FIG. 2, includes a distal delivery orifice 18 having a male luer fitting 20 to facilitate connection to a catheter hub or needle hub. A proximal end of the syringe barrel 12 is provided with a flange 22. An end view of the of the flange 22 is illustrated in FIG. 2A.

The sliding member 14 is shown in further detail in FIGS. 3 and 4. The sliding member 14 includes a threaded through bore 28 and a second unthreaded bore 30 having a diameter slightly larger than that of the threaded bore 28. The sliding member 14 is slidable on the syringe barrel 12 between a first position at which the first threaded hole is aligned with the syringe barrel for precise delivery of a material from the syringe and a second position at which the second hole is aligned with the syringe barrel for filling of the syringe or to stop delivery. The sliding member 14 also includes side rails 34 and an end stop or tab 36. The sliding member 14 is received on the flange 22 of the syringe barrel 12 such that the flange is received between the side rails 34 of the sliding member and the sliding member can slide back and forth along the flange. The ability of the sliding member 14 to slide with respect to the barrel 12 allows either the threaded bore 28 or the unthreaded bore 30 to be axially aligned with the syringe barrel 12. Accordingly, the syringe 10 can be used as a conventional syringe when the unthreaded bore 30 is aligned with the syringe barrel 12 and can be used as a threaded syringe for a more precisely controlled fluid delivery when the threaded bore 28 is aligned with the syringe barrel 12. The threaded syringe allows the delivery of higher viscosity compositions in a precisely controlled manner.

The sliding member 14 also includes a spring element 40 shown in FIG. 5 which is threaded into a side bore 42 in the sliding member. The side bore 42 is positioned at an angle A from a line which is transverse to the direction of sliding. The angle A is between about 10 and about 60 degrees, preferably between about 20 and about 40 degrees, and most preferably about 30 degrees. The spring element 40 includes a threaded casing which contains a spring and a movable ball element 44.

The threaded plunger 16 as shown in FIG. 2, includes a plunger handle 48 connected to a shaft 50. The shaft 50 includes a threaded portion 52 and an unthreaded portion 54. A distal end of the plunger 16 includes a resilient fluid tight member 56. The threaded portion 52 of the plunger is provided with a longitudinal groove 60 which cuts through the plunger threads as shown in FIG. 2B. The longitudinal groove 60 is preferably a V-shaped groove which encompasses an angle B of about 30 to about 60 degrees, preferably approximately 90 degrees. The ball element 44 of the spring element 40 is configured to be received in the groove 60 of the threaded plunger 16. The inter-engagement of the spring element 40 and the longitudinal groove 60 provide a tactile and/or audible indication to the clinician. With the longitudinal groove 60 as shown in the drawings, the clinician will feel and/or hear a click of the syringe plunger 16 for each rotation of the plunger 16. Other arrangements of the groove 60 may be provided to provide a tactile or audible indication at frequencies other than one click per rotation. For example, every other thread may be provided with a transverse notch to provide tactile indications for every two rotations.

The syringe assembly 10 according to the present invention provides a mechanism by which the syringe can be filled with fluid in the normal fashion with the plunger shaft 50 positioned in the unthreaded bore 30 of the sliding member 14. After filling, the sliding member 14 can be slid to a second position at which the plunger shaft 50 is positioned in the threaded bore 28 and the threaded plunger is used for slow, controlled injection of fluid by rotation of the plunger. In order to slide the sliding member 14 from the first position to the second position, the plunger 16 should be positioned with the unthreaded portion 54 of the plunger shaft 50 located at the intersection of the bores 28, 30 in the sliding member 14. The groove 60 and spring element 40 provide a tactile and/or audible indication or click upon each revolution of the threaded plunger 16. This allows the clinician to determine the amount of fluid injected without looking at the syringe graduation lines.

The sliding member 14 is also used as a quick stop mechanism. The sliding member 14 provides a pressure relief mechanism by which the injection pressure can be removed from the material in the syringe barrel 12 stopping injection of the material. For example, when a liquid embolic composition is delivered to a vascular site by the syringe 10 according to the present invention, the composition will continue to be delivered for a time period of about 30 seconds after the rotation of the plunger handle 48 has been halted. This is due to the back pressure in the syringe and catheter. The sliding member 14 allows the pressure on the composition to be immediately removed by moving the sliding member to a position at which the unthreaded bore 30 is aligned with the plunger 16. The use of the sliding member 14 reduces the time between the time at which the rotation of the handle 48 is stopped and the time at which material delivery from the distal end of the catheter stops to about 1 second. This time may be called the bleed out time. Thus, the bleed out time is reduced by use of the quick stop from more than 10 seconds to less than 5 seconds.

FIG. 6 shows a syringe 110 according to the present invention which includes a syringe barrel 112, a sliding member 114, and a threaded plunger 116. The syringe barrel 112 includes a distal delivery orifice 118 for connection to a catheter or needle and a proximal end of the syringe barrel is provided with a flange 122.

The sliding member 114 is shown in further detail in FIGS. 7 and 8. The sliding member 114 includes a threaded through bore 128 and a second unthreaded bore 130. The sliding member 114 also includes side rails 134 and an end stop or tab 136. The sliding member 114 is received on the flange 122 of the syringe barrel 112 such that the flange is received between the side rails 134 of the sliding member and the sliding member can slide back and forth along the flange. The ability of the sliding member 114 to slide with respect to the barrel 112 allows either the threaded bore 128 or the unthreaded bore 130 to be axially aligned with the syringe barrel 12.

The sliding member 114 is preferably provided with a thumb pad 170 at each side of the sliding member for ease of movement of the sliding member by the thumb or other fingers of the clinician. The thumb pads 170, one of which is shown in FIG. 9, are preferably formed of different colors and/or different shapes for visual and for tactile indication of the position of the sliding member. The thumb pads 170 may be attached to the sliding member 114 or may be formed as a part of the sliding member.

The sliding member 114 also includes a spring element 140 shown in FIG. 10 which is placed onto a protruding flange 172 partially surrounding the threaded bore 128 of the sliding member. The spring element 140 or clip includes a retaining end 174 which retains the spring element on the flange 172 and a plunger contacting hook end 176.

The threaded plunger 116, as shown in FIG. 6, includes a plunger handle 148 connected to a shaft 150. A distal end of the plunger 116 includes a resilient fluid tight member in the form of two O-rings 156. The threaded portion of the plunger 116 is provided with a longitudinal groove which cuts through the plunger threads. The longitudinal groove is preferably a V-shaped groove. The hook end 176 of the spring element 140 is configured to be received in the groove of the threaded plunger 116. The inter-engagement of the hook end 176 of the spring element 140 and the longitudinal groove provide a tactile and/or audible indication to the clinician of the advancement of the plunger. This allows the clinician to determine the amount of fluid injected without looking at the syringe graduation lines.

The syringe according to the present invention is particularly designed for controlled delivery of high viscosity compositions. High viscosity compositions include compositions having viscosities of about 150 to about 2000 centistokes. The syringe of the present invention may be used for delivery of a variety of compositions including liquid embolic compositions, any oncological drug, contrast agents, and the like.

High viscosity liquid embolic compositions are defined as compositions containing more than eight weight percent of a polymer, and preferably with at least twelve percent polymer as described in U.S. patent application Ser. No. 09/574,379, entitled "Novel High Viscosity Embolizing Compositions," filed May 19, 2000. It should be understood that the syringe may also be used for delivering other high viscosity fluid compositions or for delivery of fluids where it is important to provide carefully controlled liquid injection.

Examples of liquid embolic compositions and delivery systems are described in U.S. Pat. Nos. 5,830,178 and 5,695,480 which are incorporated herein by reference in their entirety.

The threaded syringes 10, 110 according to the present invention, are particularly designed for use in delivery of a high viscosity liquid embolic composition to a vascular site. The embolic composition is loaded into the syringe by positioning the sliding member with the unthreaded bore aligned with the plunger and withdrawing the plunger to draw the liquid embolic composition into the syringe barrel. The sliding member is then moved so that the threaded bore is aligned with the syringe plunger for delivery of the liquid embolic composition. The syringe is then connected to a catheter in preparation for delivery of the composition to the vascular site. Alternatively, the syringe may be formed with an attached catheter.

A distal end of a delivery catheter is positioned at the vascular site in a known manner either before or after attachment of the syringe. The embolizing composition is then injected by rotating the syringe handle. Injection of the embolizing composition forms a nidus of embolizing composition within the vascular site. Delivery of the embolizing composition is continued under known visualization techniques for a period of time or until embolization of the vascular site is complete. The injection of the embolizing composition is then halted by stopping the rotation of the syringe handle and also by sliding the sliding member so that the plunger is aligned with the unthreaded bore and pressure is released from the embolizing composition in the syringe. In the event that it is determined that additional embolizing composition is required at the vascular site, the sliding member may be moved back to position the threaded bore aligned with the plunger and delivery of the embolizing composition may be continued. The sliding member allows delivery to be stopped and started precisely any number of times until embolization is complete.

While the invention has been described in detail with reference to the preferred various changes and modifications can be made and equivalents employed, without departing from the present invention.

What is claimed is:

1. A syringe comprising:
    a cylindrical syringe barrel having an axis, a distal delivery orifice, and a proximal end;
    a sliding member positioned on the proximal end of the syringe barrel, the sliding member having an opening made up of a first threaded hole in communication with a second hole and being slidable on the syringe barrel between a first position, at which the first threaded hole is aligned with the axis of the syringe barrel, and a second position, at which the second hole is aligned with the syringe barrel; and a threaded plunger positioned within the syringe barrel for delivery of a fluid from the syringe barrel through the delivery orifice, said threaded plunger comprising a plunger shaft in axial alignment with the axis of the syringe barrel, at least a portion of said plunger shaft having threads sized to engage the threads of the first threaded hole;

wherein said plunger shaft passes through the opening in said sliding member, and wherein the sliding member at said first position allows the syringe to be used as a threaded syringe for precisely controlled fluid delivery and the sliding member at said second position allows the syringe to be used as a conventional syringe.

2. The syringe of claim 1, wherein the sliding member is slidable from the first position to the second position with respect to the threaded plunger to release pressure on a material in the syringe and stop delivery of the material from the syringe.

3. The syringe of claim 1, wherein the sliding member in the second position allows the threaded plunger to move longitudinally in the syringe barrel without rotation.

4. The syringe of claim 3, wherein the sliding member in the first position allows the threaded plunger to move longitudinally in the syringe barrel in a precisely controllable manner by rotation of the threaded plunger.

5. The syringe of claim 1 in combination with a catheter for delivery of a material in the syringe into the vascular system.

6. The combination of claim 5, further comprising a liquid embolic composition contained in the syringe for delivery to the vascular system.

7. A syringe comprising:

a cylindrical syringe barrel having an axis, a distal delivery orifice, and a proximal end;

a threaded sliding member positioned on the proximal end of the syringe barrel, the threaded sliding member having a first threaded hole and a second hole and being slidable on the syringe barrel between a first position at which the first threaded hole is aligned with the axis of the syringe barrel and a second position at which the second hole is aligned with the axis of the syringe barrel; and a threaded plunger for delivery of a fluid from the syringe barrel through the delivery orifice, said plunger having an axis and being substantially coaxial with respect to said syringe barrel, wherein the sliding member at said first position engages said threaded plunger to provide a threaded syringe for controlled fluid delivery and wherein the sliding member at said second position allows the syringe to be used as a conventional syringe.

* * * * *